(12) United States Patent
Glidden et al.

(10) Patent No.: US 9,962,443 B2
(45) Date of Patent: May 8, 2018

(54) CELLULAR ACTIVITY TARGETED NANOPARTICLE SYSTEM AND METHODS OF PRODUCING THE NANOPARTICLE SYSTEM

(71) Applicant: LA JOLLA NANOMEDICAL. Inc., Rancho Santa Fe, CA (US)

(72) Inventors: Paul F. Glidden, San Diego, CA (US); Steven Oldenburg, San Diego, CA (US)

(*) Notice: Subject to any disclaimer, the term of this patent is extended or adjusted under 35 U.S.C. 154(b) by 0 days. days.

(21) Appl. No.: 15/267,697

(22) Filed: Sep. 16, 2016

(65) Prior Publication Data

US 2017/0072055 A1    Mar. 16, 2017

Related U.S. Application Data

(60) Provisional application No. 62/219,566, filed on Sep. 16, 2015.

(51) Int. Cl.
| | |
|---|---|
| *B82Y 30/00* | (2011.01) |
| *A61K 41/00* | (2006.01) |
| *B82Y 5/00* | (2011.01) |
| *A61K 47/69* | (2017.01) |

(52) U.S. Cl.
CPC ...... *A61K 41/0052* (2013.01); *A61K 47/6929* (2017.08); *B82Y 5/00* (2013.01); *B82Y 30/00* (2013.01)

(58) Field of Classification Search
CPC .................................. B82Y 5/00; B82Y 30/00
See application file for complete search history.

(56) References Cited

U.S. PATENT DOCUMENTS

| | | |
|---|---|---|
| 6,165,440 A | 12/2000 | Johnson |
| 6,344,272 B1 | 2/2002 | Nuyta |
| 6,375,634 B1 | 4/2002 | Carroll |
| 6,530,944 B2 | 3/2003 | West et al. |
| 6,685,730 B2 | 2/2004 | West et al. |
| 6,955,639 B2 | 10/2005 | Hainfeld et al. |
| 7,018,395 B2 | 3/2006 | Chen |
| 7,510,555 B2 | 3/2009 | Kanzius |
| 7,608,240 B2 | 10/2009 | Buzatu et al. |
| 7,627,381 B2 | 12/2009 | Kanzius et al. |
| 7,638,139 B2 | 12/2009 | Peyman |
| 7,824,660 B2 | 11/2010 | Buzatu et al. |
| 7,834,331 B2 | 11/2010 | Ben-Yakar et al. |
| 7,964,214 B2 | 6/2011 | Peyman |
| 7,999,161 B2 | 8/2011 | Oraevsky et al. |

(Continued)

OTHER PUBLICATIONS

Patra et al, Fabrication of Gold Nanoparticlesw for Targeted Therapy in Pancreatic Cancer, Adv Drug Deliv Rev, Mar. 5, 2010, 62(3), 346-361.*

(Continued)

*Primary Examiner* — Carlos A Azpuru
(74) *Attorney, Agent, or Firm* — Merle W. Richman, Esq.

(57) ABSTRACT

Embodiments of nanoparticle systems and methods of producing nanoparticle systems configured to target particular cellular activity in an animal or human including a signaling pathway expression of mammal cellular activity and treat cells producing the targeted cellular activity by exposing the nanoparticle system to electromagnetic radiation in a predetermined range of wavelengths. Other embodiments may be described and claimed.

20 Claims, 3 Drawing Sheets

(56) References Cited

U.S. PATENT DOCUMENTS

| | | |
|---|---|---|
| 8,033,977 B2 | 10/2011 | Hainfeld et al. |
| 8,119,165 B2 | 2/2012 | Peyman |
| 8,137,698 B2 | 3/2012 | Peyman |
| 8,197,471 B1 | 6/2012 | Tersigni |
| 8,323,686 B2 | 12/2012 | Mirkin et al. |
| 8,323,694 B2 | 12/2012 | Hainfeld |
| 8,399,751 B2 | 3/2013 | Lu et al. |
| 8,465,484 B2 | 6/2013 | Davalos et al. |
| 8,481,082 B2 | 7/2013 | Peyman |
| 8,568,781 B2 | 10/2013 | Rademacher et al. |
| 8,668,935 B2 | 3/2014 | Peyman |
| 8,697,129 B2 | 4/2014 | Qian et al. |
| 8,709,488 B2 | 4/2014 | Peyman |
| 8,770,203 B2 | 7/2014 | Bourke, Jr. et al. |
| 8,784,895 B2 | 7/2014 | Messersmith et al. |
| 8,795,251 B2 | 8/2014 | Peyman |
| 8,801,690 B2 | 8/2014 | Peyman |
| 8,808,268 B2 | 8/2014 | Peyman |
| 8,814,860 B2 | 8/2014 | Davalos et al. |
| 8,821,940 B2 | 9/2014 | Harris et al. |
| 8,834,933 B2 | 9/2014 | Harris et al. |
| 8,932,636 B2 | 1/2015 | Peyman |
| 8,968,705 B2 | 3/2015 | Bayes et al. |
| 8,969,318 B2 | 3/2015 | Toleikis et al. |
| 8,999,294 B2 | 4/2015 | Chen et al. |
| 9,017,729 B2 | 4/2015 | Peyman |
| 9,061,056 B2 | 6/2015 | Harris et al. |
| 9,095,625 B2 | 8/2015 | Bogdanov |
| 9,211,419 B2 | 12/2015 | Krishnan et al. |
| 9,216,155 B2 | 12/2015 | Thaxton et al. |
| 9,233,157 B2 | 1/2016 | Peyman |
| 9,249,334 B2 | 2/2016 | Oldenburg et al. |
| 9,283,275 B2 | 3/2016 | Vo-Dinh et al. |
| 9,289,491 B2 | 3/2016 | Peyman |
| 9,302,087 B2 | 4/2016 | Peyman |
| 9,302,116 B2 | 4/2016 | Vo-Dinh et al. |
| 9,320,719 B2 | 4/2016 | Messersmith et al. |
| 9,320,813 B2 | 4/2016 | Peyman |
| 9,333,259 B2 | 5/2016 | Almutairi et al. |
| 9,339,557 B2 | 5/2016 | Choi et al. |
| 2007/0054290 A1 | 8/2007 | McMahon et al. |
| 2012/0190975 A1 | 7/2012 | Chen et al. |
| 2014/0296836 A1 | 10/2014 | Shen et al. |

OTHER PUBLICATIONS

Hong et al, Targeting Cancer Stem Cells by Using the Nanoparticles, Int J Nanomedicine, 2015, 10lSpec Iss):251-260.*

Melancon et al. "Cancer theranostics with near-infrared light-activatable multimodal nanoparticles," Acc Chem Res, Aug. 17, 2011 (Aug. 17, 2011). vol. 44, pp. 947-956.

Marches et al. "Specific thermal ablation of tumor cells using single-walled carbon nanotubes targeted by covalently-coupled monoclonal antibodies," Int J Cancer, Dec. 15, 2009 (Dec. 15, 2009), vol. 125, pp. 2970-2977.

Moasser, M. "The oncogene HER2: its signaling and transforming functions and its role in human cancer Pathogenesis," Oncogene, Apr. 30, 2007 (Apr. 30, 2007), vol. 26, pp. 6469-6487.

Olsen et al. "Hedgehog-interacting protein is highly expressed in endothelial cells but down-regulated during angiogenesis and in several human tumors," BMC Cancer, Aug. 4, 2004 (Aug. 4, 2004), vol. 4, pp. 1-11.

International Search Report for parent PCT Application PCT/US2016/052196 filed Feb. 12, 2016—dated Dec. 2, 2016—11 pages.

* cited by examiner

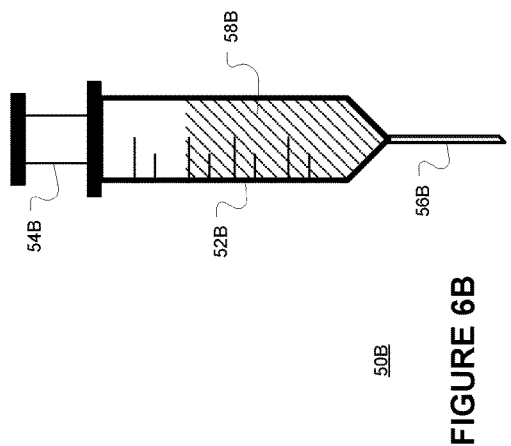
FIGURE 5
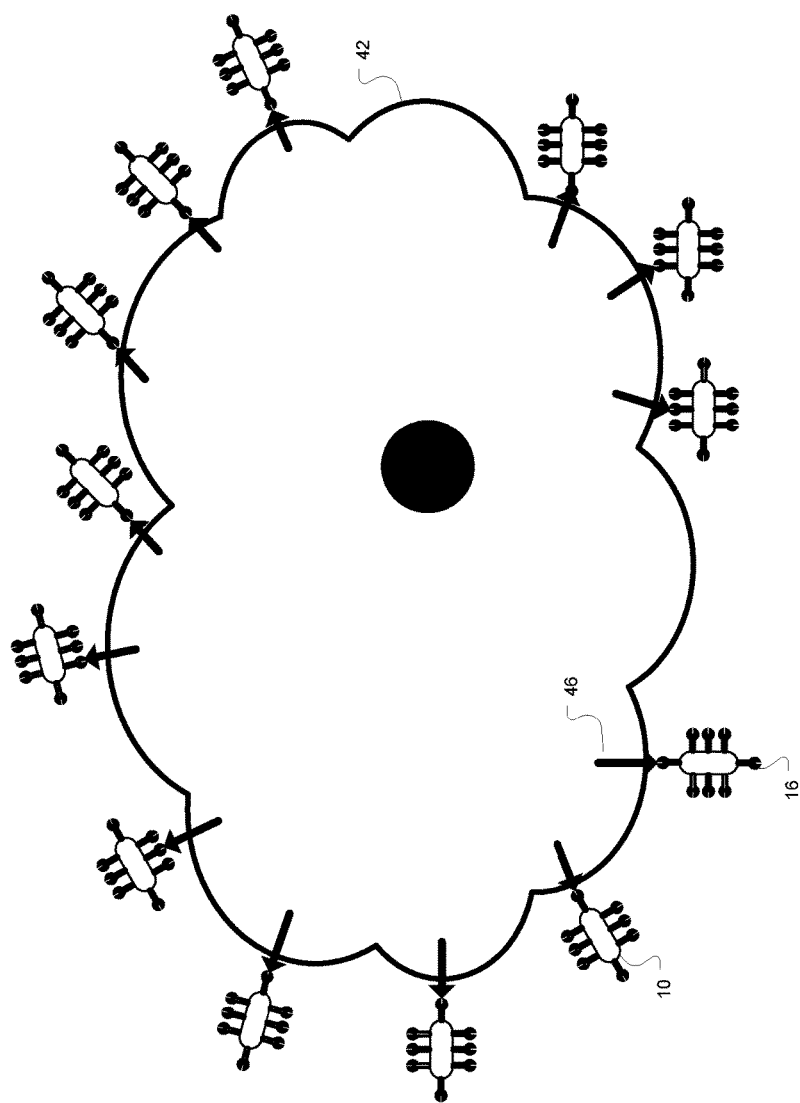
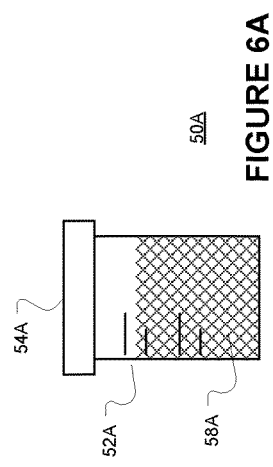
FIGURE 6A
FIGURE 6B

CELLULAR ACTIVITY TARGETED NANOPARTICLE SYSTEM AND METHODS OF PRODUCING THE NANOPARTICLE SYSTEM

CROSS REFERENCE TO RELATED APPLICATIONS

This application is a non-provisional conversion of provisional application No. 62/219,566, filed Sep. 16, 2015, entitled "A CELLULAR ACTIVITY TARGETED NANOPARTICLE AND METHODS OF PRODUCING THE NANOPARTICLE", which is incorporated by reference.

TECHNICAL FIELD

This invention is directed to nanoparticles that may be employed to visualize tissue or cells and treat tissue or cells to cause necrosis or induce apoptosis in an animal or human tissues and methods for producing the nanoparticles.

BACKGROUND INFORMATION

It may be desirable to introduce nanoparticles into an animal or human to cause tissue or cells at or near the nanoparticles to be visualized or effected in a desired way. A desired cell or tissue effect may include causing cell or tissue damage sufficient to cause cell or tissue necrosis.

BRIEF EXPLANATIONS OF THE DRAWINGS

FIG. 5 is a simplified diagram of nanoparticle systems coupled directly or indirectly to a target cell's binding sites according to an embodiment of the present invention.

FIG. 6A is a simplified diagram of a vial storage system according to an embodiment of the present invention.

FIG. 6B is a simplified diagram of a syringe storage system according to an embodiment of the present invention.

DETAILED DESCRIPTION

Figure 3A:
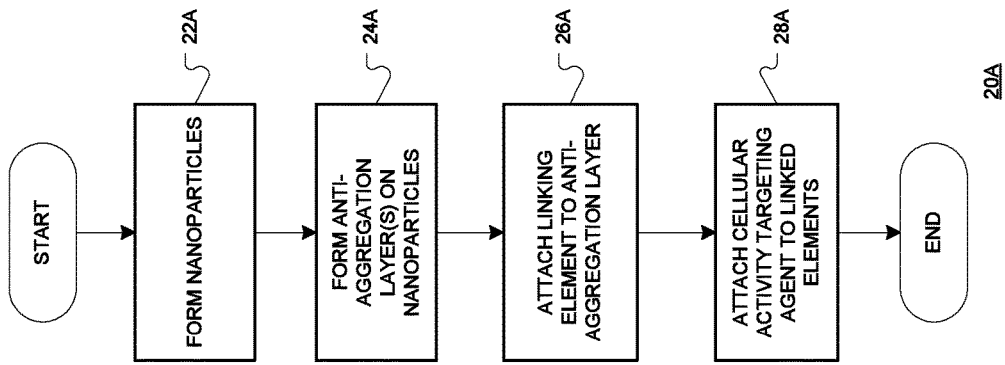
FIG. 3A is a flow diagram illustrating several methods of producing a nanoparticle system according to various embodiments.

Cellular based lifeforms employ or undergo various cellular activities during their life including during development and stasis. The cellular activities may include desired and undesired activities. An undesired cellular activity may include cancerous cellular activity including tumor growth. In an embodiment of the present invention, cancerous cells or other non-desirable cells may be visualized, controlled, damaged, or destroyed by targeting certain cellular activity. In an embodiment, a nanoparticle may include elements that bind to a particular proteins expressed by a cell. In one embodiment, nanoparticles may be deployed in a mammal body to target certain cells where the cells are to be visualized or effected in a desired way. In an embodiment, a desired cell effect may include causing cell damage sufficient to cause cell or tissue necrosis, either immediately or subsequent to treatment.

Certain cellular activities in a mammal may be controlled or monitored by certain signal pathways. The signal pathways may enable, start, control, or end certain cellular activities. In certain cancers including brain, skin, and bladder cancer, a signaling pathway including oncogene elements may be present. The signal pathway may express proteins in the cell where the expressed proteins may form binding sites that may be targeted by an agent including an antibody. It is noted the proteins expressed by undesired cellular activity may be over-expressed proteins since their related activities are not desired and thus over-expressed. Oncogene pathways use cellular activities that generate over-expressed proteins. Accordingly in order to target certain undesired cells the oncogene pathway's cellular activity may be targeted by a targeting agent. In an embodiment, a targeting agent may bind to oncogene pathway over-expressed proteins.

Different cells may use different forms of oncogene pathways including Hedgehog (HH) driven pathways. Oncogene and HH-driven pathways describe the cellular cascade that induces or forms tumors in some cancers where the pathways generate over-expressed proteins as part of the cellular cascade. HH driven pathways may be used by specific undesired cell types including Basal cell carcinomas (BCCs) in addition to some brain, other skin, and bladder cancers. HH driven pathways cellular activity also generate over-expressed proteins where these proteins may be specific to HH driven pathways including HH Smoothened, HH Patched, and HH Interacting Protein (HHIP). The HH Smoothened, HH Patched, and HH Interacting Protein (HHIP) may be transmembrane protein components. Accordingly, in order to target BCC in addition to some brain, other skin, and bladder cancers, their HH-driven pathways cellular activity may be targeted by a targeting agent. In an embodiment, the targeting agent may bind to a HH-driven pathway's over-expressed proteins including HH Smoothened, HH Patched, and HH Interacting Protein (HHIP).

In an embodiment, nanoparticle systems 10 are formed that target undesired cellular activity generated by BCCs, other cancerous cells, other hyperplastic cells, other non-cancerous tumors, or other undesired cells. The nanoparticles may target an expression of the cellular activity. In certain undesired cellular activities, the formed nanoparticles may target an expression of a signal pathway. In a further embodiment, the formed nanoparticles may target a protein expression of the signal pathway where the protein expression may be an over-expressed protein. The signal pathway over-expressed proteins to be targeted may include oncogene pathway over-expressed proteins. The signal pathway over-expressed proteins to be targeted may more particularly include HH-driven pathway over-expressed proteins. As noted, a HH-driven pathway's over-expressed proteins including HH Smoothened (Smo), HH Patched, and HH Interacting Protein (HHIP). Accordingly, the formed nanoparticle systems may target over-expressed proteins in an embodiment.

In an embodiment, a targeting agent 16 of a nanoparticle system 10 may configured or selected to couple or bind to certain cellular activity. The targeting agent 16 may be configured, selected, or engineered to bind on an over-expressed protein of an undesired cell in an embodiment. The over-expressed protein may be a component of an undesired cell's signaling pathway. The undesired cell's signaling pathway may be an oncogene pathway or more particularly a HH-driven pathway. In an embodiment, the targeting agent 16 may include an antibody configured, selected, or engineered to bind on an over-expressed protein of an undesired cell. Accordingly, a nanoparticle system 10 employing such a targeting agent or element(s) 16 may become bound to an over-expressed protein of an undesired cell. The over-expressed protein may include a binding site or cell receptor that a targeting agent or element(s) 16 may bind.

In an embodiment, targeted undesired cell(s) may include basal cell carcinomas (BCC) and squamous cell carcinomas (SCC). A nanoparticle system 10 according to an embodiment may target a cellular activity of a BCC or SCC including an over-expressed protein. In an embodiment, a nanoparticle system 10 may include a metallic core nanoparticle 12 that may be coupled or bound to one or more targeting agents or element(s) 16 via a coupler or binder 14. As noted in an embodiment a targeting agent or element(s) 16 may include antibodies that may become bound to certain cellular activity components including over-expressed proteins of a cell pathway. The targeting agent or element(s) 16 may include antibodies that may become bound cellular activity components a BCC or SCC including over-expressed proteins. The over-expressed proteins may be components of a HH-driven pathway including Smo proteins, Patched proteins, and HHIP. In an embodiment a targeting agent or element(s) 16 may include anti-HHIP antibodies that bind to HHIP.

In an embodiment, nanoparticles 12 bound to a targeting agent or element(s) 16 (nanoparticle systems 10) may be intravenously injected into a patient where undesired cell(s) are to be targeted. Nanoparticle systems 10 may also be injected into or adjacent undesired cell(s) to be targeted. In an embodiment, nanoparticles 12 bound to a targeting agent or element(s) 16 may also be injected intradermally to target certain skin cell(s) including BCC and SCC. In an embodiment, nanoparticle systems 10 may be suspended in a biologically acceptable aqueous solution (58A in FIG. 6A and 58B in FIG. 6B) to enable intravenous, intradermal, or other desired placement or delivery. The aqueous solution may be required to have a minimal viscosity to prevent nanoparticle systems 10 from settling in the solution. In an embodiment, an aqueous solution (58A in FIG. 6A and 58B in FIG. 6B) may include saline and viscosity increasing elements including polyethylene glycol (PEG) or other long chain compounds.

Once nanoparticle systems 10 are inserted into a patient, they may migrate to cellular activity targets and become bound to a cellular activity target over a period of time or a predetermined period of time as a function of their insertion location relative to the undesired cells. Once inserted in a patient however, nanoparticle systems 10 may aggregate, potentially limiting their desired movement toward undesired cells or away from desired cells. In an embodiment, a nanoparticle system 10 may include an anti-aggregation layer or shell 13. The anti-aggregation layer 13 may be located between a metallic nanoparticle 12 and targeting agent(s) 16 in an embodiment. The targeting agent 16 may be covalently bound to the anti-aggregation layer 13 in an embodiment. A covalent binding agent, element or compound 14 may covalently bind targeting agent(s) 16 to an anti-aggregation layer 13. In an embodiment, an anti-aggregation layer 13 may include silica ($SiO_2$). In the anti-aggregation layer, silica $SiO_2$ may be coupled to other elements including aluminum atoms to reduce potential an anti-aggregation layer 13 dissolution in certain environments including suspension in an aqueous solutions.

In an embodiment, nanoparticles 12 may be formed of electrically conductive materials including silver, gold, other metals, alloys, inducible electrically conductive materials, or other electrically conductive materials. The nanoparticles 12 may be formed to exhibit a desired plasmonic resonance where the particles have a strong optical response at a wavelength that is dependent on the nanoparticles' material, size and shape. The nanoparticles 12 may also scatter or absorb an imaging system's energy enabling their location in a mammal to easily be resolved.

The nanoparticles 12 may become heated when irradiated by electromagnetic radiation tuned to its plasmonic resonance where the electromagnetic radiation causes oscillations of the nanoparticle's electron cloud, resulting in heat production. The heated nanoparticles 12 may become hot enough to damage nearby, bound, or adjacent cells. The cell damage may cause immediate cell death (necrosis) or lead to eventual cell death (for example, through apoptosis induction). In an embodiment, a targeting agent or element(s) 16 may be coupled or linked to the nanoparticles 12 via different anti-aggregation layers 13, elements 14, or mechanisms where the targeting agent or element(s) 16 targets particular cellular activity including cellular signaling pathway components. As noted, the targeted cellular activity may include its signaling pathway components where the signaling pathways may employ certain proteins. The targeting agent 16 may target a cells' signaling pathway proteins where the proteins may function as a binding site or receptor for certain targeting agents 16.

Figure 1:
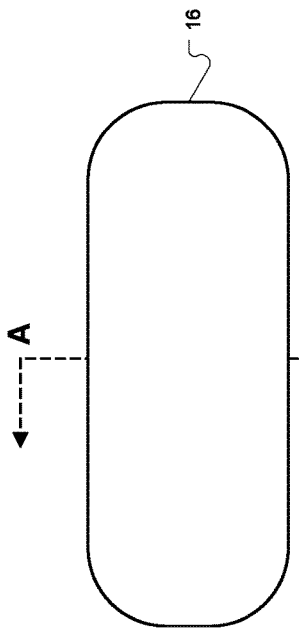
FIG. 1 is a simplified diagram of a nanoparticle system configured to target particular cellular activity according to an embodiment of the present invention.
Figure 2:
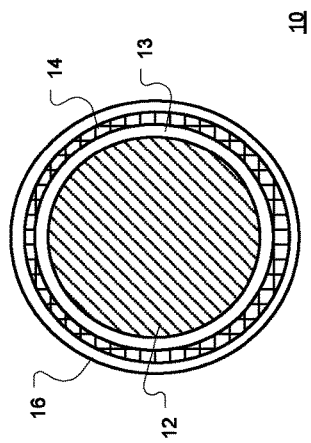
FIG. 2 is a simplified cross-sectional diagram of the nanoparticle system across line A-A of FIG. 1 according to an embodiment of the present invention.
Figure 3C:
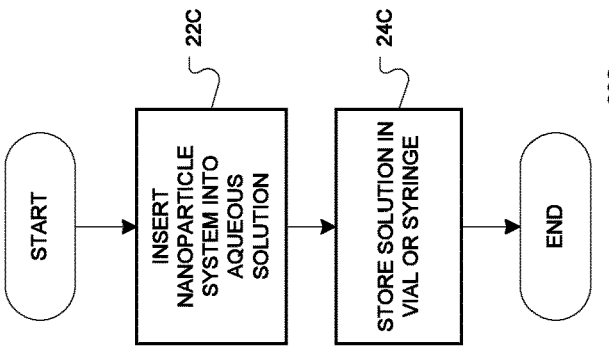
FIG. 3C is a flow diagram illustrating several methods of producing storable aqueously suspended nanoparticle systems according to various embodiments.
Figure 3B:
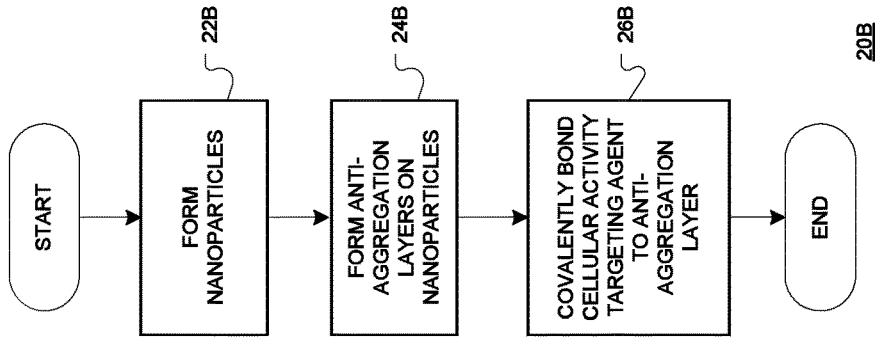
FIG. 3B is a flow diagram illustrating several methods of producing another nanoparticle system according to various embodiments.

FIG. 1 is a simplified diagram of a nanoparticle system 10 configured to target particular cellular activities according to an embodiment of the present invention. FIG. 2 is a simplified cross-sectional diagram of a nanoparticle system 10 across line A-A of FIG. 1. FIG. 3A is a flow diagram illustrating several methods of producing a first nanoparticle system 10 according to various embodiments. FIG. 3B is a flow diagram illustrating several methods of producing another nanoparticle system 10 according to various embodiments. As shown in FIGS. 1 and 2, a targeted nanoparticle system 10 may include a nanoparticle 12 coupled to targeting agents 16. It is noted that the nanoparticle system 10 shown in FIGS. 1 and 2 may have various shapes and the size relationship between the nanoparticle 12, anti-aggregation layer 13, linking layer or elements 14, and targeting agent layer or element(s) 16 may vary and not be to scale. In an embodiment, one or more anti-aggregation layer(s) or shell(s) 13 may be formed on a nanoparticle 12. In an embodiment, targeting agents 16 may be coupled to an anti-aggregation layer 13 via linkers or linker elements 14 where the targeting agents 16 and linker elements 14 are shown as layers in FIG. 2.

As noted, targeting agents 16 may be employed to target particular cellular activity. The cellular activity may be controlled, regulated, or initiated by one or more signaling components in a signal pathway. The signaling elements may include one or more proteins and the signal pathway may be an oncogene pathway including a HH-driven pathway. A targeted nanoparticle system 10 may target a cell by targeting its signal pathway including proteins. The proteins may be over-expressed proteins and may be employed in an oncogene pathway such as a Hedgehog-driven pathway. In an embodiment, targeting agents 16 may be linked directly to an electrically conductive nanoparticle 12 or an anti-aggregation layer 13. Targeting agents 16 may be covalently coupled to a nanoparticle 12 or an anti-aggregation layer 13 directly via covalent binder 14.

In another embodiment, a targeting agent 16 may be linked to a nanoparticle 12 or anti-aggregation layer 13 via a covalent or non-covalent linking agent 14. In the algorithms 20A and 20B shown in FIGS. 3A and 3B, nanoparticles 12 having desired size and electrically conductive properties may be formed (activities 22A, 22B). The nanoparticles 12 may be silver nanoplates, silica coated silver nanoplates, gold nanoshells, silver nanoshells and gold nanorods (GNR) in an embodiment. In an embodiment, the nanoparticle 12 may be biologically inert.

The formed nanoparticles 12 may be shaped to support plasmonic resonance within a predetermined range of wavelengths. In an embodiment, when electromagnetic radiation producing wavelength(s) within a predetermined range of wavelengths stimulates a nanoparticle 12, the nanoparticle's temperature may increase due to oscillations of its electrons. In an embodiment, a nanoparticle 12 may be shaped to absorb or scatter electromagnetic radiation when irradiated by wavelengths ranging from 400 nm to 1500 nm. In another embodiment, a nanoparticle 12 may be configured to absorb or scatter electromagnetic radiation when irradiated by wavelengths ranging from 700 nm to 1400 nm. In a further embodiment, a nanoparticle may be shaped to absorb or scatter electromagnetic radiation when irradiated by wavelengths ranging from 750 nm to 1100 nm.

In an embodiment, a laser may be employed to irradiate nanoparticle systems 10 (activity 36B of algorithm 30B). A nanoparticle 12 may be shaped to absorb or scatter electromagnetic radiation when irradiated by a laser producing energy having a wavelength about 1064 nm. In a further embodiment, a nanoparticle 12 may be shaped to absorb or scatter electromagnetic radiation when irradiated by a laser producing energy having a wavelength about 800 nm. In other embodiments, a nanoparticle 12 may be shaped to absorb or scatter electromagnetic radiation when irradiated by other energy sources including X-ray radiation sources, microwave radiation sources, focused ultrasound energy sources, radio frequency energy and other electromagnetic, magnetic, and photonic energy sources.

After forming one or more nanoparticles 12 having desired resonant, absorption, or scattering properties (activity 22A, 22B of algorithms 20A, 20B from FIGS. 3A and 3B), one or more anti-aggregation layers or shells 13 may be formed on the resultant nanoparticle 12 (activity 24A, 24B of algorithms 20A, 20B from FIGS. 3A and 3B). In an embodiment, an anti-aggregation layer 13 may include a silica ($SiO_2$) complex. The $SiO_2$ complex may reduce nanoparticle system 10 aggregation when employed. The $SiO_2$ complex may be modified to include other components. As noted, a nanoparticle system 10 may be delivered and stored in an aqueous solution (58A in FIG. 6A and 58B in FIG. 6B). The aqueous solution may include water, saline, viscosity modifiers and other elements that may dissolve some $SiO_2$ complexes. A different $SiO_2$ complex including a complex with aluminum atoms may be formed to limit or reduce dissolution in various aqueous solutions.

In an embodiment, an anti-aggregation layer 13 may consist of $SiO_x(OH)_y$, wherein $x+y \leq 4$ and x is $\geq 1$. In another embodiment, an anti-aggregation layer 13 may consist of $SiO_a(OH)_bR_c$, wherein $a+b+c \leq 4$, a is $\geq 1$ and R is a chemical group having a carbon atom that is directly bonded to a silicon atom. In another embodiment, an anti-aggregation layer 13 may consist of $AlO_m(OH)_n$, wherein $m+n \leq 6$ and m is $\geq 1$. In an embodiment, the R groups may consist of all carbon or be a mixture of carbon and other atoms such as hydrogen, nitrogen, sulfur and/or oxygen. In an embodiment, the R group may comprise a molecule group chosen from a group consisting of an amine, a thiol, a carboxylic acid, an azide, an aldehyde, an epoxide and combinations thereof.

In an embodiment, an anti-aggregation layer 13 may be formed on a nanoparticle 12 via condensation. In particular, a SiO complex may be formed on a nanoparticle 12 via a condensation reaction in a solution containing at least one silane having a chemical formula given by $X_nSiY_{(4-n)}$, wherein $0<n<4$, and wherein one or both of X and Y is selected from the group consisting of OEt, OMe, Cl, Br, I, H, alkyl, fluoroalkyl, perfluoroalkyl, alkoxide, aryl, alkyl amine, alkyl thiol and combinations thereof. In a further embodiment, at least one silane is selected from the group consisting of aminopropyltriethoxy silane, aminopropyltrimethoxy silane, mercaptopropyltriethoxysilane, mercaptopropylmethoxysilane, tetramethoxy silane, tetraethoxy silane, and combinations thereof.

It is noted that forming an anti-aggregation layer 13 including silicon oxides via condensation using various silane precursors may allow different chemical functionalities to be integrated into the resultant silicon oxide shell 13. A chemical functionality may include targeting agents 16 such as antibodies that target signaling pathway components or certain other cellular activity. As noted, incorporating aluminum atoms into the molecular network of the silicon oxide complex of an anti-aggregation layer 13 may dramatically increase its stability in some aqueous solutions. In an embodiment, aluminum atoms may be included in a $SiO_2$ complex by exposing the complex to a solution having an aluminum salt dissolved therein. In an embodiment, the aluminum salt may include aluminum chloride. It is noted that targeting agents 16 may also remain bound to the surface of aluminum stabilized silicon oxide anti-aggregation layers or shells 13 for extended periods of time.

In an embodiment, a linking element 14 may be coupled to the nanoparticle 12 or an anti-aggregation layer or shell 13 (when formed thereon) (activity 26A of algorithm 20A). Then a cellular activity targeting agent or element(s) 16 may be linked to the nanoparticle 12 or an anti-aggregation layer via linking elements 14 (activity 28A of algorithm 20A). In another embodiment, a cellular activity targeting agent 16 may be covalently bound to a nanoparticle 12 or an anti-aggregation layer or shell 13 (when formed thereon) via a covalent binder 14 (activity 26B of algorithm 20B).

In activity 26A of algorithm 20A, a linking element or agent 14 may be attached or applied to the nanoparticles 12 or an anti-aggregation layer or shell 13 (when formed thereon). In an embodiment, the linking agent 14 may be a thiolated linker including lipoic acid or methyl polyethylene glycol sulfydryl (mPEG-SH). Such a linking agent 14 may form a base layer that gives carboxylic acid functionality to subsequently bind to targeting agents 16 (activity 26A). The resultant carboxylic acid functionality may also subsequently bind to a targeting agent 16 including one or more proteins.

In an embodiment, a linking agent 14 carboxylic acid functionalization may be achieved via a thiol or amine+ linker molecule+carboxylic acid group. Further, a linker agent 14 molecule can be formed from a carbon chain or include a polyethylene glycol (PEG) molecule. In a further embodiment, a linking agent 14 may include other heterobifunctional linkers.

As noted in an embodiment, cellular activity targeting agent 16 may be covalently bound to a nanoparticle 12 or an anti-aggregation layer or shell 13 (when formed thereon) via a covalent binder 14 (activity 26B of algorithm 20B). In an embodiment, the covalent binder 14 molecules are polymers. In an embodiment, the covalent binder 14 molecules are one or more types of polyethylene glycol (PEG). PEG comprises a linear oligomer of ethylene glycol of the form $(-CH_2CH_2O-)_x$ where x is in the range of 2 to 2000 and the $CH_2CH_2$ groups are linked in a chain. In an embodiment, the covalent binder 14 may include a mixture of functionalized PEG molecules and non-reactive PEG molecules. In a further embodiment, the PEG molecules may include a mixture of methoxy PEG (PEG-OMe) and carboxylic acid PEG (PEG-COOH) and the ratio between PEG-OMe and PEG-COOH may be in the range of 1:1 to 1:2, 1:1 to 1:3, 1.1 to 1:5, 1:1 to 1:10, 1:1 to 1:100, 1:3 to 1:10, 1:3 to 1:50, or 1:5 to 1:50.

It is noted that in a covalent binder 14 including PEG molecules, each end of a PEG molecule may have an affinity for amines on an aluminum silicate surface (an anti-aggregation layer or shell 13) and each other end of the PEG molecule may have an affinity for a free thiol group of an antibody or other cellular activity targeting agent 16. It is noted in other embodiments that the cellular activity targeting agent(s) 16 may be attached to an anti-aggregation layer or shell 13 surface via any linker 14 providing a stable physical or chemical association to the anti-aggregation layer or shell 13 surface directly or indirectly by any suitable means including via covalent bond, non-covalent bond, electrostatic charge and the like.

To improve direct cellular activity targeting agent(s) 16 attachments to an anti-aggregation layer or shell 13 surface via any linker 14, the anti-aggregation layer or shell 13 surface coating may be modified. The anti-aggregation layer or shell 13 surface coating may be modified by functional organic molecules with reactive groups such as thiols, amines, carboxyls, and hydroxyl. The surface active reactants may include, but are not limited to, aliphatic and aromatic amines, mercaptocarboxylic acid, carboxylic acids, aldehydes, amides, chloromethyl groups, hydrazide, hydroxyl groups, sulfonates and sulfates to accommodate such direct linkages As noted, a cellular activity pathway targeting agent 16 may target cellular activities that are part of a signaling pathway. The targeting agent may target components of the signaling pathway. The signaling pathway may be an oncogene pathway and the targeted components may be proteins, effectively over-expressed proteins. The targeting agent 16 may be configured, selected, or engineered to bind to a signal pathway component including a protein. Further in an embodiment, the oncogene pathway may be a specific pathway, a Hedgehog-driven signaling pathway. In such an embodiment, targeting agent 16 may target an expressions or components of the Hedgehog-driven signal pathway including a protein expression. In an embodiment, HH-driven pathway expressed proteins to be targeted may include Smoothened (Smo) protein, Patched protein, and HHIP. The targeting agent 16 may be configured, selected, or engineered to bind to a HH-driven pathway expressed Smoothened (Smo) protein, Patched protein, and HHIP.

FIG. 5 is a simplified diagram of an application 40 of nanoparticle systems 10 where the nanoparticle systems 10 are bound via targeting agent 16 to a protein expression 46 of a cell 42 according to an embodiment of the present invention. The protein expressions 46 may be receptors or other forms that may be bound by the targeting agent 16 in an embodiment. As shown in FIG. 5, a nanoparticle system's 10 targeting agent 16 may become bound to a cell's 42 protein expression 46. The protein expression 46 may be a cellular activity of cell 42 that may be part of its signaling pathway. In an embodiment, the protein expression 46 is an over-expressed protein and may be a component of an oncogene pathway. In an embodiment, the protein expression 46 is an over-expressed protein and may be a component of an HH-driven pathway. The protein expression 46 may be a HH Smoothened protein, HH Patched protein, or HHIP. In an embodiment, the protein expression may a BCC signaling pathway component. It is noted that FIG. 5 is not to scale and that the nanoparticle systems 10 may be 1000 times smaller than the target cell 42 in an embodiment. It is further noted that the targeting agent 16 are equally small and thus its physical volume minute compared to the cells 42. Further where the targeting agent 16 includes an antibody, its volume present in nanoparticle systems 10 is significantly smaller than a therapeutic dose required to treat cells 42, in an embodiment, at least 3 orders of magnitude smaller.

In an embodiment, a targeting agent 16 may include a peptide aptamer, an antibody, or an antibody fragment (for example, Fab fragment). Such a targeting agent 16 may target and become bound to proteins expressed by targeted cellular activity (including signal pathway components or expressions). In another embodiment, a targeting agent 16 may include nucleic acid. Such a targeting agent 16 may also target and become bound to proteins expressed by targeted cellular activity (including signal pathway components or expressions). In a further embodiment, a targeting agent 16 may include a Ribonucleic acid (RNA) aptamer. Such targeting agent 16 may target and become bound to proteins expressed by targeted cellular activity (including HH-driven or other signal pathway components or expressions).

In a further embodiment, a targeting agent 16 may include a small molecule including cyclopamine or other small molecule known to have high affinity for elements of the HH-driven pathway expressions. Such a targeting agent 16 has been shown to target and become bound to proteins expressed by targeted cellular activity (including HH-driven or other signal pathway components or expressions). In another embodiment, a targeting agent 16 may include a T-cell. The T-cell may target and become bound to proteins expressed by targeted cellular activity (including HH-driven or other signal pathway components or expressions). In an embodiment, the particular mammal cellular activity to be targeted may include cancerous cellular activity.

As noted, the particular mammal cellular activity to be targeted may include basal cell carcinoma (BCC) activity. In such an embodiment, a nanoparticle system 10 may be capable of specifically binding directly or indirectly to BCC protein expressions or other cellular activity. In such an embodiment, nanoparticle systems 10 not bound to basal cell carcinoma cells may move to other surrounding tissues, creating a potential contrast between the density of nanoparticle systems 10 bound to BCC and the lack of unbound nanoparticle systems 10 in the surrounding tissues.

As noted in an embodiment, one or more nanoparticle systems 10 may be introduced into a mammal to be treated via an aqueous solution. In such an embodiment, nanoparticle systems 10 may be suspended in an aqueous solution (activity 22C of algorithm 20C shown in FIG. 3C). The aqueous solution (58A in FIG. 6A and 58B in FIG. 6B) with suspended nanoparticle systems 10 may be stored in a vial (52A of FIG. 6A) or a syringe (52B of FIG. 6B) in an embodiment (activity 24C). FIG. 6A is a simplified diagram of a vial storage system 50A according to an embodiment of the present invention. As shown in FIG. 6A, an aqueously suspended nanoparticle systems 10 solution 58A may be stored in a vial 52A. The vial may have a sealed, puncturable lid 54A to enable extraction via a syringe or other device. FIG. 6B is a simplified diagram of a syringe storage system 50B according to an embodiment of the present invention. As shown in FIG. 6B, an aqueously suspended nanoparticle systems 10 solution 58B may be stored in a syringe 52B. The syringe 52B may include a plunger 54B and a needle 56B. The syringe 52B may be employed to deliver the aqueously suspended nanoparticle systems 10 58B intradermally, subcutaneously, intravenously, or directly into a cancerous or non-cancerous tumor or area of hyperplasia in an embodiment.

Figure 4B:
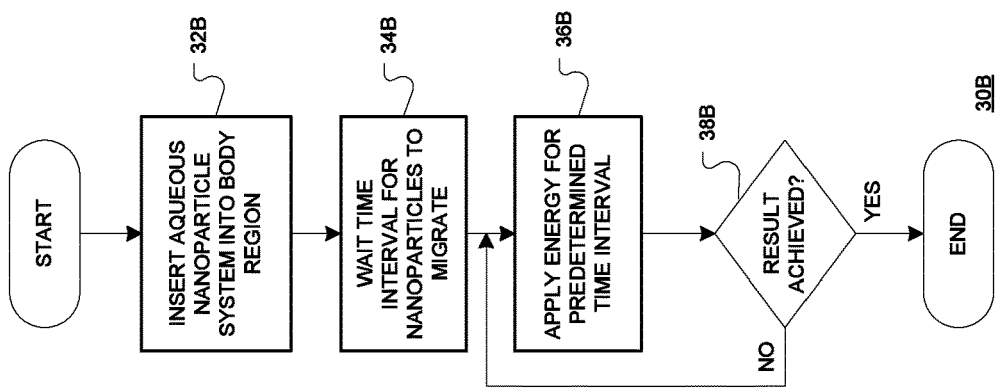
FIG. 4B is a flow diagram illustrating several methods of employing nanoparticle systems to desirably affect targeted cell(s) according to various embodiments.
Figure 4A:
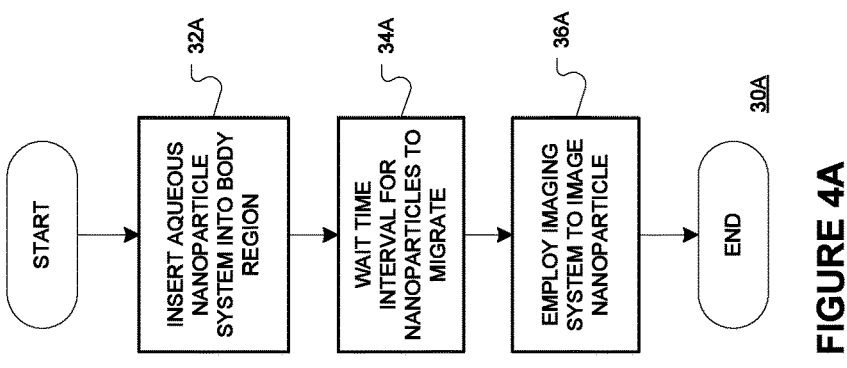
FIG. 4A is a flow diagram illustrating several methods of employing nanoparticle systems to image targeted cell(s) according to various embodiments.

In an embodiment, the algorithm 30A shown in FIG. 4A may be employed to use nanoparticle systems 10 to visualize cellular targets and algorithm 30B shown in FIG. 4B may be employed to use nanoparticle systems 10 to damage or kill cellular targets. As shown in FIGS. 4A and 4B, nanoparticle systems 10 suspended in an aqueous solution (58A, 58B) may be inserted into a body region (activity 32A, 32B) where the nanoparticle systems 10 may migrate to and bind to target cells. In both algorithms 30A, 30B, a predetermined time interval may be allowed for the nanoparticle systems 10 to migrate to target cells and bind to the cells (activity 34A and 34B). If a user desires to visualize cells that have been bound to nanoparticle systems 10, they may employ a imaging system that causes the nanoparticle systems 10 to be easily seen due to the nanoparticle system's 10 high electromagnetic radiation absorption or scattering (as function of frequency and energy type) (activity 36A of FIG. 4A). A user may employ an imaging device to verify nanoparticle systems 10 are bound to desired cells prior to applying energy to the nanoparticle systems 10 that may cause the nanoparticle systems 10 to generate heat (activity 36B of FIG. 4B).

In an embodiment, a practitioner may apply electromagnetic radiation energy at or near target cells to be treated. The electromagnetic radiation may include energy at frequencies at or near the plasmonic resonance of nanoparticle systems 10. The electromagnetic radiation may be provided at an energy level for a predetermined time interval (activity 36B) sufficient to heat exposed nanoparticle systems 10 to a temperature that may damage or kill target cells. In an embodiment, a practitioner or user may repeat activity 36B until a desired result is achieved (activity 38B). A practitioner may determine that a desired result has been achieved by visualizing the target cell damage (with or without an imaging system).

It may be possible to execute the activities described herein in an order other than the order described. Various activities described with respect to the methods identified herein can be executed in repetitive, serial, or parallel fashion. The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. A nanoparticle system for effecting undesired cells in a mammal, the nanoparticle system including:
    a nanoparticle comprised of an at least partially electrically conductive material and shaped to become heated to effect undesired cells when exposed to electromagnetic radiation in a predetermined range of wavelengths; and
    a targeting agent covalently coupled to the nanoparticle, the targeting agent selected to target a signaling pathway expression of the undesired cells.

2. The nanoparticle system for effecting undesired cells in a mammal of claim 1, wherein the signaling pathway expression is a protein expression and the targeting agent is selected to bind to the protein expression.

3. The nanoparticle system for effecting undesired cells in a mammal of claim 2, wherein the signaling pathway expression is an oncogene pathway expression.

4. The nanoparticle system for effecting undesired cells in a mammal of claim 2, wherein the signaling pathway expression is a Hedgehog-driven pathway expression.

5. The nanoparticle system for effecting undesired cells in a mammal of claim 4, wherein the Hedgehog-driven pathway expression is one of Smoothened, Patched, and Hedgehog Interacting Protein (HHIP) and the targeting agent is selected to bind to the one of the Smoothened, Patched, and Hedgehog Interacting Protein (HHIP).

6. The nanoparticle system for effecting undesired cells in a mammal of claim 4, wherein the Hedgehog-driven pathway expression is a Hedghog interacting protein (HHIP) and the targeting agent is selected to bind to the HHIP.

7. The nanoparticle system for effecting undesired cells in a mammal of claim 1, wherein the nanoparticle includes one of silver nanoplates, gold nanoshells, and gold nanorods.

8. The nanoparticle system for effecting undesired cells in a mammal of claim 1, wherein the nanoparticle system further includes an anti-aggregate layer coupled to the nanoparticle, the anti-aggregate layer including a silica complex and wherein the targeting agent is covalently coupled to the anti-aggregate layer.

9. The nanoparticle system for effecting undesired cells in a mammal of claim 8, wherein the targeting agent is covalently bonded to the anti-aggregate layer via a linking agent.

10. The nanoparticle system for effecting undesired cells in a mammal of claim 2, wherein the targeting agent includes one of a peptide aptamer, an antibody, and an antibody fragment configured to bind to the protein expression.

11. The nanoparticle system for effecting undesired cells in a mammal of claim 2, wherein the targeting agent includes one of a nucleic acid, a ribonucleic acid (RNA) aptamer, and a small molecule configured to bind to the protein expression.

12. The nanoparticle system for effecting undesired cells in a mammal of claim 2, wherein the nanoparticle is shaped to become heated when exposed to electromagnetic radiation having a wavelength from 700 and 1400 nm.

13. The nanoparticle system for effecting undesired cells in a mammal of claim 1, wherein the undesired cells include basal cell carcinoma cells.

14. A nanoparticle system targeted to a Hedgehog-driven pathway expression of mammal basal cell carcinoma cellular activity, the nanoparticle system including:
   a nanoparticle comprised of an at least partially electrically conductive material; and
   a targeting agent covalently coupled to the nanoparticle, the targeting agent selected to target a Hedgehog-driven pathway expression of mammal basal cell carcinoma cellular activity.

15. The nanoparticle system targeted to a Hedgehog-driven pathway expression of mammal basal cell carcinoma cellular activity of claim 14, wherein the Hedgehog-driven pathway expression is one of a Smoothened, Patched, and Hedgehog Interacting Protein (HHIP) and the targeting agent is selected to bind to the one of the Smoothened, Patched, and Hedgehog Interacting Protein (HHIP).

16. The nanoparticle system targeted to a Hedgehog-driven pathway expression of mammal basal cell carcinoma cellular activity of claim 14, wherein the Hedgehog-driven pathway expression is a Hedgehog Interacting Protein (HHIP) and the targeting agent is selected to bind to the HHIP.

17. The nanoparticle system targeted to a Hedgehog-driven pathway expression of mammal basal cell carcinoma cellular activity of claim 14, wherein the nanoparticle includes one of silver nanoplates, gold nanoshells, and gold nanorods.

18. The nanoparticle system targeted to a Hedgehog-driven pathway expression of mammal basal cell carcinoma cellular activity of claim 14, the nanoparticle system further including an anti-aggregate layer coupled to the nanoparticle, the anti-aggregate layer including a silica complex and wherein the targeting agent is covalently coupled to the anti-aggregate layer.

19. The nanoparticle system targeted to a Hedgehog-driven pathway expression of mammal basal cell carcinoma cellular activity of claim 18, wherein the targeting agent is covalently bonded to the anti-aggregate layer via a linking agent.

20. The nanoparticle system targeted to a Hedgehog-driven pathway expression of mammal basal cell carcinoma cellular activity of claim 14, wherein the targeting agent includes one of a peptide aptamer, an antibody and an antibody fragment configured to bind to the protein expression.

* * * * *